US008633171B2

(12) United States Patent
Luo et al.

(10) Patent No.: US 8,633,171 B2
(45) Date of Patent: Jan. 21, 2014

(54) TRANSPARENT OIL GELLING SYSTEM

(75) Inventors: Dexin Luo, Fresh Meadows, NY (US);
Tian Xiang Wang, Dix Hills, NY (US);
Tatyana R. Tabakman, Brooklyn, NY (US); Shahan Nazar, Garden City, NY (US); Steven Hasher, Blue Point, NY (US); Joseph Gubernick, New York, NY (US)

(73) Assignee: ELC Management, LLC, New York, NY (US)

( * ) Notice: Subject to any disclaimer, the term of this patent is extended or adjusted under 35 U.S.C. 154(b) by 197 days.

(21) Appl. No.: 12/890,108

(22) Filed: Nov. 9, 2010

(65) Prior Publication Data

US 2011/0052734 A1 Mar. 3, 2011

Related U.S. Application Data

(63) Continuation-in-part of application No. 10/985,781, filed on Nov. 10, 2004, now abandoned.

(60) Provisional application No. 60/519,583, filed on Nov. 13, 2003.

(51) Int. Cl.
*A01N 43/04* (2006.01)
*A61K 31/715* (2006.01)
*A01N 37/00* (2006.01)
*A61K 31/21* (2006.01)
*A01N 31/00* (2006.01)
*A61K 31/045* (2006.01)

(52) U.S. Cl.
USPC ............. 514/54; 514/506; 514/738; 514/724; 424/401

(58) Field of Classification Search
USPC ................. 514/54, 506, 738, 724; 424/401
See application file for complete search history.

(56) References Cited

U.S. PATENT DOCUMENTS

| | | | |
|---|---|---|---|
| 4,226,889 A * | 10/1980 | Yuhas | 424/59 |
| 5,093,111 A | 3/1992 | Baker et al. | |
| 5,478,552 A | 12/1995 | Hasegawa | |
| 5,849,275 A | 12/1998 | Calello et al. | |
| 5,961,998 A | 10/1999 | Arnaud et al. | |
| 6,019,962 A | 2/2000 | Drechsler et al. | |
| 6,036,947 A | 3/2000 | Barone et al. | |
| 6,042,842 A * | 3/2000 | Lemann et al. | 424/401 |
| 6,340,466 B1 | 1/2002 | Drechsler et al. | |
| 6,555,097 B1 | 4/2003 | Rabe et al. | |
| 6,821,942 B2 | 11/2004 | Sebillotte-Arnaud et al. | |
| 2003/0134761 A1 | 7/2003 | Sebillotte-Arnaud et al. | |
| 2003/0171479 A1 | 9/2003 | Lennon | |

FOREIGN PATENT DOCUMENTS

| | | |
|---|---|---|
| DE | 847901 | 8/1952 |
| EP | 0648496 | 4/1995 |
| EP | 1172095 | 1/2002 |
| EP | 1277463 | 1/2003 |
| EP | 1325729 | 7/2003 |
| EP | 1792607 A1 * | 6/2007 |
| JP | 59-122415 | 7/1984 |
| JP | 05-221829 | 8/1993 |
| JP | 06-256141 | 9/1994 |
| JP | 06-263618 | 9/1994 |
| JP | 07-033625 | 2/1995 |
| JP | 11-255616 | 9/1999 |
| JP | 11-349441 | 12/1999 |
| JP | 2000-226315 | 8/2000 |
| JP | 2002-087929 | 3/2001 |
| JP | 2001-187715 | 7/2001 |
| JP | 2001-279040 | 10/2001 |
| JP | 2002-003340 | 1/2002 |
| JP | 2002-138017 | 5/2002 |
| JP | 2002-187811 | 7/2002 |
| JP | 2003-095846 | 4/2003 |
| JP | 2003-113021 | 4/2003 |
| JP | 2003-277228 | 10/2003 |
| JP | 2003-277231 | 10/2003 |
| JP | 2004-137226 | 5/2004 |
| JP | 2004-210720 | 7/2004 |
| JP | 2004-292373 | 10/2004 |
| JP | 2004-300093 | 10/2004 |
| JP | 2005-068056 | 3/2005 |
| WO | WO-98/30193 | 7/1998 |
| WO | WO-99/06473 | 2/1999 |

OTHER PUBLICATIONS

PCT International Search Report; International Application No. PCT/US04/37016; Completion Date: Apr. 28, 2005; Date of Mailing: Jun. 1, 2005.
PCT Written Opinion of the International Searching Authority, or The Declaration; International Application No. PCT/US04/37016; Completion Date: Apr. 28, 2005; Mailing Date: Jun. 1, 2005.
Supplemental European Search Report; EP04819057.3; Completion Date: Jul. 19, 2007; Date of Mailing: Jul. 27, 2007.

* cited by examiner

*Primary Examiner* — Kendra D Carter
(74) *Attorney, Agent, or Firm* — Cynthia R. Miller

(57) ABSTRACT

The invention relates to a gellant system for a polar oil comprising gellant effective amounts of silica, a sugar fatty acid ester and a long chain polymer. The gellant system of the invention is useful in gelling polar oils to produce transparent or translucent gels useful in topical compositions.

15 Claims, 3 Drawing Sheets

TRANSPARENT OIL GELLING SYSTEM

CROSS REFERENCE

This is a continuation-in-part of Ser. No. 10/985,781, filed Nov. 10, 2004 now abandoned, claiming priority from Provisional Application Ser. No. 60/519,583, filed Nov. 13, 2003.

FIELD OF THE INVENTION

The invention relates to the field of cosmetics. More specifically, the invention relates to a gelling system for cosmetic oils, and compositions comprising a polar oil and a gellant system for the polar oil.

BACKGROUND OF THE INVENTION

When women are asked what cosmetic item they simply could not be without, a typically high percentage reply that lip color is an essential item of their beauty wardrobe. With a product that is so widely used by the cosmetic-purchasing public, it is not surprising that there is a continuing demand for new and innovative product types. Among the current trends for lip products are those that remain in place for several hours without the need for reapplying, as well as those that provide a high level of gloss and shine. In many cases, it is highly desirable to combine these two characteristics. While there is a considerable variety of products of these types currently available, the commercially available products frequently suffer from certain drawbacks with a similar root problem. For example, the long-wearing products on their own can be drying and uncomfortable on the lips, with a dull finish, thereby requiring a moisturizing topcoat to be applied over them. Such topcoats, however, are difficult to formulate, since they need to be sufficiently incompatible with the base coat, which is frequently based on non-polar hydrocarbons and silicones, to prevent interference with the base coat's wear, and at the same time, are preferably transparent to give the best level of glossy appearance to the lips. Typically, however, the currently available topcoat products are opaque sticks that produce a small amount of shine. Similarly, with lip gloss products intended to provide high shine, it is difficult to achieve the desired level of transparent gloss without producing a product that is too liquid or oily. The problem in producing the perfect product lies in the difficulty of gelling the cosmetic oils that constitute the backbone of the majority of lip products. The most commonly used oils are typically polar, and achieving the desired level of viscosity and clarity is a complex matter. Although it is of course possible to gel such oils, the usual viscosifying agents employed are waxes and/or clays; the end product achieved with the use of such materials is typically either too opaque or else less viscous and more oily-feeling that would be desired. Thus there continues to be a need for a soft liquid gel-type product that does not convey an oily feeling on the lips, yet provides a significant level of transparency that will improve the gloss and shine of the final product. The present invention now provides a solution to this need.

SUMMARY OF THE INVENTION

The present invention relates to clear (e.g., transparent or translucent) liquid gel compositions for topical application to the skin, the compositions comprising a polar oil, and a gellant system for the polar oil, the gellant system comprising a silica and a sugar fatty acid ester in a ratio of the silica to the sugar fatty acid ester in a range of from about 10:0.5 to about 0.5:5.0, and a long chain polymer having a molecular weight in a range of from about 400 to about 10,000 Daltons, wherein particles of the silica are suspended and well-dispersed in the polar oil, the particles of silica associated with sugar rings of the sugar fatty acid ester serving as cross-linking centers, and alkyl groups of the sugar fatty acid ester entangled with the long chain polymer serving as spacers interconnecting the cross-linking centers so as to form a three-dimensional network having a crosslinking density sufficient to contain the polar oil.

The invention also relates to a method of gelling a polar oil which comprises adding to the polar oil, a gellant system for the polar oil comprising a silica and a sugar fatty acid ester in a ratio of the silica to the sugar fatty acid ester in a range of from about 10:0.5 to about 0.5:5.0, and a long chain polymer having a molecular weight in a range of from about 400 to about 10,000 Daltons, wherein particles of the silica are suspended and well-dispersed in the polar oil, the particles of silica associated with sugar rings of the sugar fatty acid ester serving as cross-linking centers, and alkyl groups of the sugar fatty acid ester entangled with the long chain polymer serving as spacers interconnecting the cross-linking centers so as to form a three-dimensional network having a crosslinking density sufficient to contain the polar oil.

The invention further relates to a method of conferring shine to a skin surface which comprises applying to the skin surface a composition comprising at least one polar oil, and a gellant system for the polar oil comprising a silica and a sugar fatty acid ester in a ratio of the silica to the sugar fatty acid ester in a range of from about 10:0.5 to about 0.5:5.0, and a long chain polymer, having a molecular weight in a range of from about 400 to about 10,000 Daltons, wherein particles of the silica are suspended and well-dispersed in the polar oil, the particles of silica associated with sugar rings of the sugar fatty acid ester serving as cross-linking centers, and alkyl groups of the sugar fatty acid ester entangled with the long chain polymer serving as spacers interconnecting the cross-linking centers so as to form a three-dimensional network having a crosslinking density sufficient to contain the polar oil.

The present invention also concerns a gellant system for a polar oil, the gellant system comprising a silica and a sugar fatty acid ester in a ratio of the silica to the sugar fatty acid ester in a range of from about 10:0.05 to about 0.5:5, and at least one long chain polymer having a molecular weight in a range of from about 400 to about 10,000 Daltons, wherein particles of the silica when suspended and well-dispersed in the polar oil, and associated with sugar rings of the sugar fatty acid ester, serve as cross-linking centers, and alkyl groups of the sugar fatty acid ester entangled with the long chain polymer serve as spacers interconnecting the cross-linking centers so as to form a three-dimensional network having a crosslinking density sufficient to contain the polar oil.

The compositions of the present invention are soft, lubricious, transparent gels, viscous liquids or pastes which are flexible and film-forming, and which are particularly well adapted for use as a glossy top coat for a transfer resistant base coat or as a high shine lip gloss on its own. Compositions of the present invention preferably contain no waxes or clays.

DETAILED DESCRIPTION OF THE INVENTION

Figure 1:
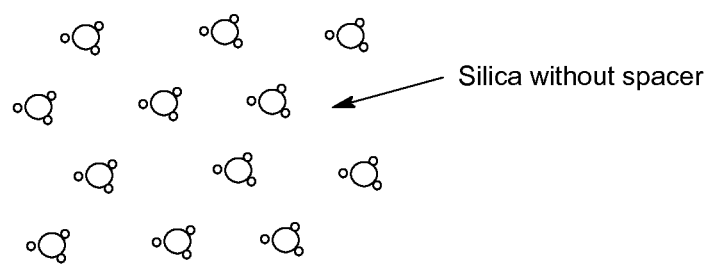
FIG. 1 is a diagram showing silica dispersed in polar oil.

The base of the compositions of the present invention is a cosmetically acceptable polar oil. The term "cosmetically acceptable" oil means one that is industry-accepted as safe for use on the skin surface to which the product is intended to be applied. Polar oils are frequent components of cosmetic compositions, and are distinguished from non-polar oils, such as hydrocarbons, by their relative lack of hydrophobicity. Polar oils typically contain heteroatoms, with higher electron negativity than carbon, e.g., alcohol residues, or an ester or triglyceride component. Examples of useful polar oils include, but are not limited to, vegetable oils and triglycerides (including hydrogenated liquid vegetable oils), such as castor oil, coconut oil, corn oil, jojoba oil, cottonseed oil, soybean oil, walnut oil, wheat germ oil, peach kernel oil, olive oil, peanut oil, sunflower seed oil, palm kernel oil, calendula oil, illipe butter, shea butter and caprylic/capric triglycerides; esters having the formula RCO—OR' wherein RCO represents a carboxylic acid radical and OR' represents an alcohol residue, such as isodecyl neopentanoate, tridecyl octanoate, cetyl palmitate, cetyl octanoate, cetyl stearate, cetyl myristate, isopropyl palmitate, isopropyl myristate, polyglyceryl-2-isostearate, neopentyl glycol distearate, isodecyl oleate, decyl isostearate, diisopropyl sebacate, PEG-4 diheptanoate, dioctyl malate, and isohexyl neopentanoate; polyol fatty acid polyesters, e.g., fatty acid polyesters derived from aliphatic or aromatic polyols that have at least 4 free hydroxyl groups, of which at least 80% of these free hydroxy groups are then esterified with one or more fatty acids having from 8 to 22 carbon atoms, preferably polyol fatty acid polyesters that are derived from sugar polyols that comprise mono-, di, and polysaccharides or sugar alcohols, e.g., the fatty acid polyester may be sucrose polycottonseedate (see U.S. Pat. No. 6,555,097, the contents of which are incorporated herein by reference); and fatty alcohols, such as lanolin alcohol, cetyl alcohol, isocetyl alcohol or oleyl alcohol. There may be a single polar oil, or a combination of polar oils, employed in the composition. The polar oils will normally constitute from about 10 to about 99% by weight of the composition, more preferably from about 30 to about 95% of the composition. When using polar oils that are solid or semi-solid, lower quantities, e.g., about 10% or less, are preferred to retain the transparent or translucent effect.

Polar oils, particularly non-silicone polar oils, are typically difficult to gel and retain the desired clarity. However, the present invention achieves a gelled polar oil, without the use of waxes or clays to thicken the polar oil, by employing a true gel system.

A true gel, e.g., an organogel, which is based on the self-assembly of structural molecules, has a three dimensional network structure composed of at least three key elements: cross-linking centers and spacers forming the network, and liquids which fill in the network. By "self-assembly", it is meant that there are two possible methods in which structural molecules can be linked to form a gel. According to one method, the self-assembling molecules go through a chemical reaction such that covalent bonds are formed among the molecules, resulting in an irreversible three-dimensional network. This kind of gel can not be reorganized or restructured until the covalent bonds are broken. Typically, gelled material is difficult to dissolve in liquids. Rather, the gelled material typically swells. The solubility of the gelled material is limited as a result of the presence of high cross-linking density and the short spacer length of the network. High cross-linking density and short spacer length greatly limit the ability of small molecules, such as solvent, to freely pass in and/or out of the network.

In a second method of self-assembly, physical reactions link the molecules to form a gel. This is the type of gel employed in the compositions of the present invention. These physical reactions are: 1) hydrogen-bonding among cross-linking centers, spacers and other functional groups on materials in the gel which are capable of hydrogen-bonding, e.g., —OH, —NH$_2$, —C(O)O—, and so forth; and 2) other physical interactions such as dipole-dipole interactions. The gels formed by these kinds of physical interactions are reversible. For example, a gel formed by dipole-dipole interactions might be decomposed by introducing other chemicals which may interfere with the dipole-dipole interactions under at certain conditions, such as dilution. In this way, a gel could be decomposed and also be re-assembled by a change in concentration. In a further example, gels formed by hydrogen-bonding interactions will be liquefied above the decomposition temperature of hydrogen-bonding and will reform as a gel after cooling below that temperature.

To achieve a desired viscosity or firmness from the gel structure, an appropriate number of cross-linking points or centers are incorporated into the structure. Cross-linking density or gel firmness is further dependent on the lengths of the spacers which link the cross-linking centers. Generally, shorter spacers and a greater number of centers result in a firmer gel having a lesser capacity to hold liquids. On the other hand, longer spacers and a lesser number of centers results in a more flexible gel having a greater capacity to hold liquids. The latter type gel, providing greater resilience, has the kind of aesthetic appeal (e.g., texture/feel) most desired by consumers of skin products, for example lip products.

True gels are distinguished from polymer thickened liquid systems. In a polymer thickened liquid system, a viscosity change is dependent on the amount of polymer added. At about 1 percent polymer concentration, polymer chains in solution act like threads or random coils and have a tendency to overlap with each other. The expansion of the threads depends on the solubility parameters of polymer and solvent. The smaller the difference in the parameters, the larger the thread will be. In other words, better solvency of the system will give an overlap of threads as at lower concentration. However, the overlap of threads in solution (as low as only 1 percent) does not provide a degree of chain entanglement sufficient to result in true gel structure, i.e., a three dimensional network. The overlap structure will never result in as firm a structure, having non-brittle and/or flexile properties, as that achieved by a true gel. The true gel structure imparts certain properties to the substrate, for example, a lip product. These properties are a combination of shear-thinning and resilience. In particular, the resilience performance is unique to gel structure. Due to the cross-linking among the centers and the spacers, shear thinning on application of the product to the lips will be limited, and the three-dimensional network will pull back as soon as the force, which deformed the network initially, is released, thus resulting in a flexible gel.

It has been discovered that, in accordance with the present invention, the key elements in the successful gelling of polar oils, while retaining considerable clarity, are a combination of at least one silica, at least one sugar fatty acid ester or ether and a long chain polymer. Although none of these materials used alone will provide the desired gelling effect, when used together, as described in more detail below, the result is a high viscosity, transparent or translucent liquid gel with excellent aesthetics for application to the lips or other skin surfaces where a clear shine or gloss is desired. While not wishing to be bound by any particular theory, it is believed that the hydroxide groups on the sugar fatty esters interact via hydrogen-bonding with the hydroxide groups on the surface of the silica particles, while the fatty acid portion of the ester molecule with its hydroxide groups entangle the polymer chains and also interact with the polar oil components of the composition. Thus, the silica particles (which are suspended in and well-dispersed in the polar oil) associated with sugar rings of the sugar fatty acid ester serve as physical cross-linking centers while the alkyl chains of the fatty ester entangled with the polymer chains act as network spacers, linking the cross-linking centers, to form a gel phase. The success in this combination is particularly surprising in view of the general lack of success previously in producing clear (i.e., a transparent or translucent) gelled polar oil.

The presence of silica, dispersed in the polar oil, in the absence of any spacers, as indicated in FIG. 1, will not result in the formation of a gel network.

Figure 2:
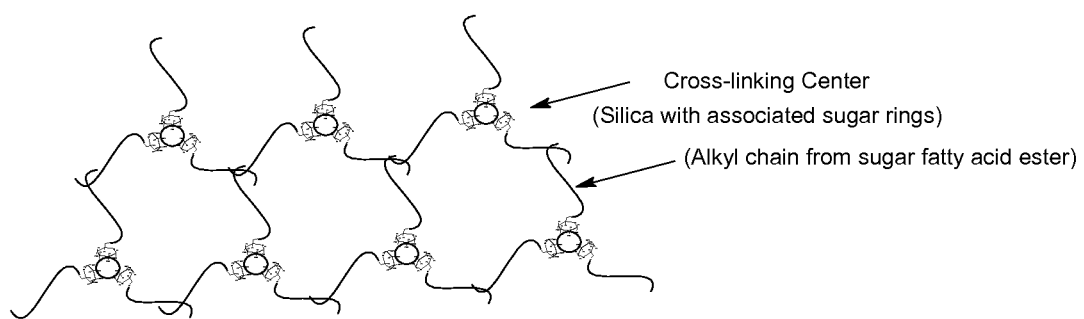
FIG. 2 is a diagram showing a gel network including short spacer moieties.

If only short spacer moieties (such as the alkyl chains of the sugar fatty acid ester) are provided, as shown in the general structure below, a gel network will be formed; however, the resulting network will have less freedom (compared to a gel made with long chain spacers) for liquid penetration and will further demonstrate both limited resilience and oil containing (absorbing) performance. Without the long chain polymer component, the gel will lack the desired degree of flexibility demanded by consumers of cosmetic lip products; instead, the formed gel will be relatively firm. Additionally, in a system lacking long polymer chains, a portion of the silica may function as a common thickener. Such a system is shown in the general structure shown in FIG. 2.

Figure 3:
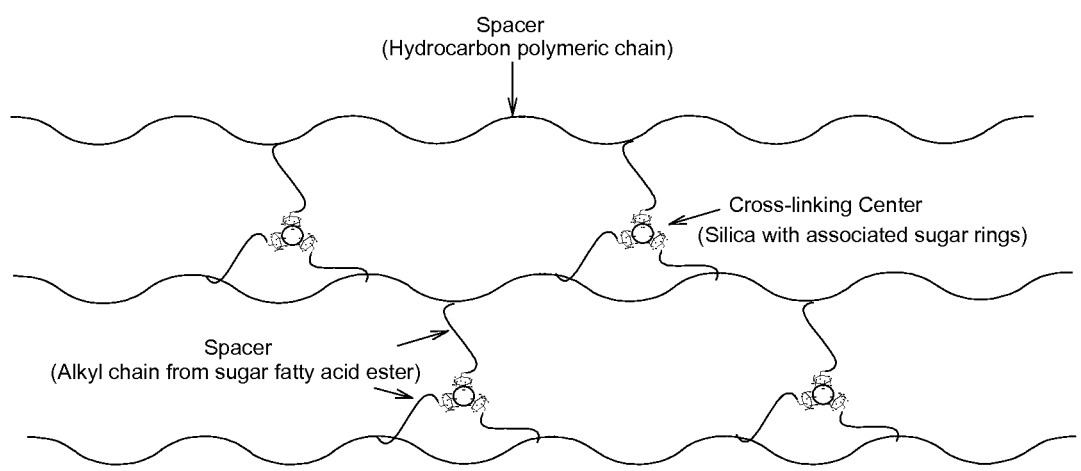
FIG. 3 is a diagram showing a gel network including long chain polymeric spacer moieties.

The presence of long chain polymeric spacers in the system, as indicated in the general structure shown in FIG. 3, results in improved resilience and oil absorbing performance of the network.

Thus, although a true gel may be formed using shorter chain polymers, to optimize the desired aesthetics of resilience and oil absorbing capacity, as demonstrated by compositions in accordance with a preferred embodiment of the present invention, the presence of one or more long chain polymers is needed in forming the three-dimensional gel network. The long chain polymers thus are useful for their resilience and oil-absorbing properties, and for conferring some additional viscosity, but they also contribute to the feel of the product. In general, they confer a greater amount of tack to the composition, which in turn results in longer wear. While all of these properties are desirable, the Applicants believe that the resilience property is particularly unique to these types of lip products; that is, heretofore, the Applicants have not been aware of any similar product demonstrating the resilience of the compositions of the present invention. A further advantage of the gels of the present invention is that sweating, a common problem associated with lipstick products, is minimized/avoided. This advantage is believed to result from the capacity of the relatively loose gel to hold more liquids (e.g., polar oil) and also because the silica may also absorb some liquid.

Thus, in accordance with a preferred embodiment, the reversible gels according to present invention are composed of three kinds of structural molecules: silica, sugar fatty acid ester and long chain polymer. The sugar rings of the ester associated with the silica form the cross-linking centers; and the alkyl chains of the sugar fatty acid ester, physically entangling with one another and with the polymer chains, form the spacers. It is believed that the gels of the present invention are formed as a result of hydrogen-bonding interactions between silica and the sugar ring portion of the sugar fatty acid ester (and other functional groups having a hydrogen-bonding capability) and the entanglement between alkyl portions of the sugar fatty acid ester and with the polymer chains. The presence of numerous hydroxide groups on the surface of silica particles and on the sugar rings of the sugar fatty acid ester maximizes the strength of the hydrogen-bonding between these two functional materials. As a result, the silica surface is associated with multiple sugar ring groups which possess alkyl chains available to entangle one another and also the polymeric, e.g., hydrocarbon, chains. Prior to the present invention, it would have been expected that non-polar hydrocarbon would not have been compatible with polar oil because of the differences in their polarities. However, by entanglement, the potential stability issue relative to the incompatibility between non-polar hydrocarbon and polar oil is solved.

In addition, the presence of the polymer provides even more possibilities for adjusting the viscosity of the gelled system and the performance characteristics of products. The viscosity of a gel system is mainly dependent upon two key elements, the population of cross-linking centers and the length of spacers between two cross-linking centers. The molecular weight of polymer, e.g., hydrocarbon, can be used to adjust the viscosity of the gel system, since, in principle, if the amount of silica in the system is constant, such that only the length of the spacer is considered, then the longer the spacer (i.e., the greater the molecular weight), the lower will be the viscosity. Alternatively, the viscosity of a desired gel system will be increased as the molecular weight of polymer is decreased (i.e., shorter spacer length). However, for the most desirable aesthetics, the molecular weight of the polymer should be large enough to permit inter-chain (physical) entanglements between the polymeric chains and the alkyl groups of the sugar fatty acid ester. As the length of polymeric chains or spacers increases, the more liquid the network can hold, which means that the viscosity of the gel is decreased. Alternatively, as the spacer length decreases, the viscosity increases and the system becomes more firm, resulting in a reduction in resilience, of oil absorbing capacity, and so forth.

Any silica particle may be used in the gelling systems of the present invention, provided the particle is not fully surface-coated (e.g., the hydroxyl groups are capable of hydrogen-bonding). Use of partially coated products, while possible, will result in the need to use higher levels of silica to achieve the desired effect. The amount of silica used is not particularly critical, and can be employed in an amount of up to about 40% by weight of the composition, although the higher levels will produce a drier, less aesthetically pleasing product, and the higher levels necessary with particles having less exposed surface area do not viscosify as well as lower levels. The preferred silica employed in the gellant component is a fumed silica. By "fumed silica" it is meant those high-surface area powdered silicas prepared by a pyrogenic process, e.g., during burning silicon tetrachloride in air (i.e., by the flame hydrolysis of silicon tetrachloride) and has a purity of 99.8% or greater. In this process, submicron sized molten spheres of silica collide and fuse to form three dimensional, branched, chain-like aggregates, of approximately 0.1 to 0.5 microns in length. Cooling takes place very quickly, limiting the particle growth and ensuring the fumed silica is amorphous. Fumed silicas are available in untreated form, or with a surface treatment to render the silica more polar or non-polar. Although any type can be used, preferably the fumed silica used in the present invention is untreated, or at most partially treated. A fumed silica fully coated with non-polar materials will not provide the desired effect, although a silica coated with polar material, such as dimethicone copolyol, may provide some utility. The surface area of the fumed silica is preferably between about 90 to about 380 m$^2$/g, and most preferably is between about 200 to about 380 m$^2$/g. A particularly useful fumed silica is commercially available from Cabot Corporation under the trade name Cab-O-Sil M-5. As a guideline, for an aesthetically pleasing product, a fumed silica is employed in an amount of about 0.2 to about 10% by weight, preferably about 1 to about 5%, of the total composition.

The sugar fatty acid ester useful in the compositions of the present invention possesses a high capability for hydrogen-bonding, and preferably is a compound obtained by reacting a saturated or unsaturated $C_{12}$-$C_{36}$ fatty acid, preferably $C_{16}$-$C_{22}$, such as $C_{18}$-$C_{22}$, with a sugar or alkylsugar in which the alkyl group contains from 1 to 8 carbon atoms. The sugar is preferably a mono- or oligosaccharide. Examples of useful mono- or oligosaccharides include, but are not limited to, glucose, sucrose, galactose, fructose, lactose, mannose, maltose, trehalose, melibiose, raffinose, or ribose. A preferred sugar fatty ester is a fatty ester of glucose or alkylglucose. The fatty acid esters of alkylglucose are ethers of glucose in which the alkyl chain comprises from 1 to 8 carbon atoms, preferably 1-4 carbon atoms. The preferred ester may contain a mixture of mono-, di-, tri- and tetraester derivatives with a proportion which may be of at least 50% by weight of mono- and diester derivatives and usually not exceeding 95% by weight of monoester derivatives relative to the total weight of the mixture. The alkyl chains of the sugar fatty acid esters will entangle the long chain polymers provided that the latter are of sufficient length. Examples of sugar fatty esters that may be used in the invention include, but are not limited to, sucrose monolaurate, glucose palmitate, alkylglucose sesquistearates, for instance methylglucose sesquistearate and alkylglucose palmitates, for instance methylglucose palmitate or ethylglucose palmitate, as well as the PEG or PPG derivatives of such compounds, for example, PEG-20 methyl glucose sesquistearate. Such compounds are widely available commercially, e.g., under the tradenames Glucate™, Glucam™, and Glucamatem (Amerchol), Grillocose™ (Grillo-Werke), and Antil™ (Goldschmidt). If used in the gels of the present invention, polyol fatty acid esters, derived from an aliphatic or aromatic polyol that has at least 4 free hydroxyl groups, will have at least 20%, and preferably up to 80% to 100%, free hydroxyl groups (i.e., not esterified with one or more fatty acids). The high polarity of the sugar fatty acid ester results in a greater degree of hydrogen-bonding with other polar functional materials in the system. The amount of the sugar fatty acid ester used in the compositions of the present invention typically may be in the range of from about 0.1 to about 10%, preferably about 0.5 to about 5%, by total weight of the composition.

Long chain polymers useful as the long spacers in forming the gel networks of the present invention, are not soluble or only partially soluble in the polar oil, and include, but are not limited to, hydrocarbon polymers, particularly high viscosity liquid or paste hydrocarbon polymers having a molecular weight of between about 400 and 10,000 Daltons, more preferably, between about 400 and 6000 Daltons, or at least $C_{12}$, more preferably $C_{12}$-$C_{16}$, and most preferably, $C_{18}$ and higher. While polymers having molecular weights greater than 6000 Daltons may be used in the compositions of the present invention, there use will tend to reduce the clarity of the product somewhat, resulting in a more translucent rather than transparent appearance. Polymers having molecular weights greater than 10,000 Daltons will tend to result in an opaque end product. The use of polymers having a molecular weight of less than 400 Daltons (i.e., less than $C_{12}$) is not recommended as their use would be expected to result in a gel demonstrating a less than desirable degree of flexibility. Additionally, polymers which are fully soluble in the polar oil will function as film formers rather than spacers. Preferred examples of polymers suitable for use in the gels of the present invention include linear or branched polybutene, polyisobutene, polyethylene, polydecene, hydrogenated derivatives thereof, and copolymers thereof, and mixtures of the foregoing. Useful, but less preferred for use in the present invention are other long chain moieties, such as polysaccharides, and structurally related starches and cellulose, i.e., Methocel and Ethocel), as well as somewhat shorter chain polyurethanes. Relatively shorter chain polymers, such as celluloses and also polyglyceryl-2-diisostearate/IPD1 copolymer, may also be used. See Example 1A herein; however, the shorter chains provide relatively shorter spacers, thus resulting in denser products (i.e., firmer, higher viscosity gel) demonstrating less than optimal flexibility/resilience polyglyceryl-2-diisostearate/IPDI copolymer and oil absorbing capacity. Polyglyceryl-2-diisostearate/IPDI copolymer may also contribute a film forming property to the end product. Particularly preferred for use in the gels of the present invention are hydrocarbon polymers, such as hydrogenated polyisobutene, as illustrated in Example 1B herein. The long chain polymer may be present in the compositions of the present invention in amounts in the range of from about 1 to about 70%, preferably from about 5 to about 50%, and most preferably in the range of from about 10 to 45%, by total weight of the composition.

As discussed herein, the performance (e.g., viscosity or firmness) of the gel will depend principally upon the number of the cross-linking centers and the length of the spacers. Also important to the properties of the end product are the ratio of silica to sugar fatty acid ester at the cross-linking centers, and the ratio of the silica to the long chain polymer. By carefully selecting the ratio of the silica to the sugar fatty acid ester, a suitable number of cross-linking centers is provided in the system which will impact upon the capacity for holding liquids and thus the viscosity/performance of the gel system.

Overall, the ratio of the silica to sugar fatty acid ester will be in the range of from about 10:0.5 to 0.5:5.0, with the lower amounts of the silica producing a lower viscosity product, and higher amounts of the silica producing a higher viscosity product. A product having a ratio of about 6:1 to 1:5, more preferably about 4.0:1.0-1:1, and most preferably about 3:1-1:1, silica to ester is particularly preferred. The ratio of silica to polymer may be in the range of from about 1:0.5-35, preferably in the range of from about 1:2.5-25, and more preferably in the range of from about 1:5-22.5. The presence of too much polymer, and in particular, too much hydrocarbon polymer, in the system may reduce the transparency of system and/or render the composition undesirably tacky.

The viscosity of the endproduct is also ultimately affected by the amount of gellant used relative to the amount of polar oil, with a higher viscosity achieved by a higher amount of gelling components. The viscosity is further affected by the polarity of the oils used, as the silica is more readily suspended in a more polar oil, presumably due to the interaction of the hydroxyl groups of the silica and the polar groups on the oils, so that a well-suspended silica can be used at smaller amounts than a silica that is not so readily suspended. The clarity of the gel may also be influenced by the amount of sugar fatty acid ester used; although a more opaque gel still provides a gel system with unique and aesthetically pleasing properties, a transparent or translucent character is still preferred. Therefore, to maintain the clarity of the final product, it is preferred that no more than about 3% sugar fatty acid ester be employed as a whole in the formulation. Clarity is also enhanced by ensuring that the silica is well-dispersed in the ester, which is achievable by the use of extended homogenization time.

Gels according to the present invention are formed by mixing together the silica and polar oil components using a homogenizer until a smooth and homogeneous (uniform) mixture is obtained. Homogenization is required to avoid the formation of agglomerates of silica (20-30 micrometers in diameter) rather than the desired particles having a diameter of about 0.2-0.3 micrometers. It is important that the silica be suspended and well-dispersed in the oil phase; otherwise, it will merely act as a thickener, an oil absorber, a stabilizer and/or a filler. It is of further importance to the formation of the gel network that the silica particles be well-dispersed in the oil prior to introducing any further components. Then, additional components of the composition are added, except for the long chain polymer and the sugar fatty acid ester, and the batch is mixed with a prop mixture at about 70 to about 100 rpm, at a temperature in the range of from about 60°-80° C., until it is completely clear. The long chain polymer component is added while mixing until the mixture is uniform and clear. The mixture is then cooled to about 50° C. (about 10° C. above the melting point of the sugar fatty acid ester), and the sugar fatty acid ester is then added to the mixture, mixed until dissolved, with continued mixing under the same temperature and mixing conditions, for several minutes (e.g., 15-30 minutes) until network formation is complete, which typically occurs at the point when all the components are dissolved. The product temperature is then lowered to room temperature or to the desired pouring temperature (e.g., about 25-30° C.). Generally, the addition of further components, such as emollients, after the ester is introduced is to be avoided. This is because such additions require heating to open the network (i.e., disrupting the H-bonding), and then cooling to close it again. Additional components may be added after the ester, if they may be added at low temperature (e.g., 35-40° C.) which will not require opening the network. Such ingredients include, for example, fragrance, preservatives, and some actives. However, it is most preferred that such ingredients be added before introducing the sugar fatty acid ester so that these other ingredients may be well-dispersed in the system. In preparing the gel, the sugar fatty acid ester, added last, serves to link together the silica particles and the long chain polymer. Thus a gel structure is formed with silica at the cross-linking centers and mainly the segments of hydrocarbon polymeric chains as long chain spacers.

The chemical structure of sugar fatty acid esters, such as methyl glucose sesquistearate, which is lipophilic at one end (non-polar hydrocarbon chain) and hydrophilic at the opposite end (sugar ring with multi-hydrophilic hydroxide groups), makes these molecules typically useful as low HLB value surfactants. Surprisingly, however, the inventors have discovered that the sugar fatty acid ester can be used as a key element of self-assembling molecules to construct a gel network. The hydroxide groups, associated with the sugar ring of the sugar fatty acid ester, are linked with silica via hydrogen-bonding, and the hydrocarbon (alkyl) chain, at the opposite end of the sugar fatty acid ester molecule is linked with the polymer, e.g., hydrocarbon polymer or non-polar polymer, chains, via inter-chain entanglement. Thus, the function of the sugar fatty acid ester in the gels of the present invention is completely different from its typical function. The sugar fatty acid ester no longer has a surfactant or plasticizer function, but acts as a building block for forming a three-dimensional network. That the sugar fatty acid ester would fit the basic requirements for the present invention; that is, a component with multiple surface hydroxide groups for maximum hydrogen-bonding possibilities with silica, and sufficiently long carbon chains for chain entangling with non-polar polymer chains, is surprising and unexpected from the prior art.

Silica, for example, fumed silica, is typically used in cosmetic products as a thickener or de-tacking material. However, silica has an entirely different and unexpected function in the present invention. Silica, dispersed uniformly in the polar oil, acts as a portion of the network cross-linking centers together with the sugar rings of the sugar fatty acid ester. The hydroxide groups on the silica surface act both as hydrogen-bonding acceptors and donors.

As discussed herein, a true gel will not form merely by mixing together the sugar fatty acid ester, the silica, and a long chain polymer component. Also necessary to the formation of the gel is the determination of an appropriate ratio of the components of the gels of the present invention; in particular, the ratio of the silica to the sugar fatty acid ester. The ratio was determined based on certain assumptions by the inventors as follows.

First, it was reasoned that, if the ratio of silica to sugar fatty acid ester, e.g., methyl glucose sesquistearate, was too small (too little silica), the formed silica-methyl glucose sesquistearate structure would result in a center with only one or two functional groups and only one or two alkyl chains, and these would need to be very long to perform as spacers since the distance between silica particles would be long, resulting in a very loose gel with insufficient mechanical performance and a lack of velvety texture. If the ratio were too high, there would be too much silica, resulting in a brittle gel with no useful mechanical performance. Additionally, the product would be too dry, as any moisture would be absorbed by the silica. Such a product could not easily be applied to the lips. Therefore, it was reasoned that the functional group number should be larger than two, since only in that situation, would formation of the gel structure be possible. Polymer chemistry dictates that a linear polymeric system will be formed if it is constructed from monomers with two kinds of functional groups, the so-called AB-type monomers. Using monomers having more than two functional groups, cross-linking will occur during polymerization and a three-dimensional network will be formed as long as there are no reaction condition changes, such as reaction temperature changes, or the introduction of chain transfer chemicals and/or mono-functional monomer, and so forth.

Second, once the viscosity is observed to dramatically increase, performance considerations (aesthetically and commercially acceptable texture/firmness) impact upon the ratio.

Third, the amount of sugar fatty acid ester (e.g., methyl glucose sesquistearate) was roughly calculated or estimated as 0.3× of the weight of silica. This estimation was based on the following: 1) the density of silica or surface area (200 $m^2/g$ for Cab-O-Sil M5); 2) the molecular weight of the methyl glucose sesquistearate (given the number of molecules for a certain mass); and 3) the estimated surface area of a sugar ring structure (given the weight of the methyl glucose sesquistearate which roughly matched the total surface area of at least 2× (400 $m^2/g$ in the present case). This ensured there will be at least 2× of sugar rings on the surface of one possible silica particle. The sugar rings with larger surface area can be associated with the smaller surface area of silica, since the silica surfaces are multi-layered. Regarding 2) and 3), above, since methyl glucose sesquistearate is a mixture of mono- and diesters of a methyl glucoside and stearic acid, the following estimations were made: Methyl glucoside: MW 194.18; Stearic Acid: MW 284.48; mono-ester MW 460.66; Di-ester MW 727.14. As methyl glucose sesquistearate is a mixture of di- and mono-ester, its MW was estimated to be between 461-727. A rough estimation for its molecular weight was taken as 600. From the density of sugar, 1.54 g/cm$^3$, it was also estimated that its surface area is about 600 m$^2$. (1.54 g/cm$^3$=1.54/10$^6$ m$^3$; estimating that the height of a chair configuration is about 10$^{-9}$ m, then the surface area is about 600 m$^2$/g—about the area of 2.5 g of the silica. From the foregoing, a ratio of about 0.3 g of methyl glucose sesquistearate per 2.5 g of silica was determined. In such a gel network, each center would have two tails (alkyl chains from the sugar fatty acid ester, or methyl glucose sesquistearate). However, to ensure the formation of a 3-dimensional network to result in a sufficiently firm gel, it was reasoned that more than 2× of functional free alkyl chains from the methyl glucose sesquistearate would be needed, or about 0.5-0.6 g of the methyl glucose sesquistearate per 2.5 g of silica, assuming that, for the determination of the molecular weight of methyl glucose sesquistearate, an average number each of di- and mono-ester of methyl glucoside and stearic aid was used, there being at least two covalent bonds per sugar ring, and, for each bond, a length of about 1.5 Å and a height of about 10 Å was estimated. It was also considered that the sugar rings on the surface of fumed silica do not lay down in a mono-layer, but in a multi-layer formation. The sugar ring has hydroxide groups which H-bond with silica but also has free hydroxide groups on the opposite side of the ring which also form H-bonds with another sugar ring. Thus, the determination of the ratio leads to unexpected results attributable to the Applicants' selection, and is not easily derived from the prior art. Table 1, below illustrates the change in viscosity resulting from the combination of the various components forming the gel network.

TABLE 1

| | | Viscosity (cps)[+] | |
| --- | --- | --- | --- |
| | Caprylic/Capric Triglyceride | Castor Oil | Sucrose Poly Cottonseedate |
| 1 Pure Chemical Viscosity | 25.0 | 750.0 | 400.0 |
| 2 97.0 g pure chemical plus 2.5 fumed silica | 1060 | 1200 | 1500 |
| 3 99.0 pure chemical plus 1.0 g Methyl glucose sesquistearate | 130 | 1100 | 900 |
| 4 100.0 g (2) plus 1.0 g Methyl glucose sesquistearate | 4400 | 15,900 | 19,000 |

[+]The viscosity was measure by using Brookfield RVT viscometer; spindle A, 10 rpm, 1.0 min.

Table 1 illustrates that three-dimensional gel networks are formed rather than polymer-thickened liquid systems. Such high viscosities, as shown in the final row (4) of the table would not be achievable were these not true gels. While neither the silica nor the methyl glucose sesquistearate will gel the polar oil without the other, the combination of silica and methyl glucose sesquistearate increases the viscosity of the polar oil dramatically, even in the absence of a long chain polymer spacer component; the silica and sugar fatty acid ester forming the cross-linking centers, and the alkyl tails of the ester providing short spacers. It is not possible to reach the high viscosities shown in row 4 of the table using only 2.5% silica, and it is therefore also clear from row 4 of the table that the methyl glucose sesquistearate is not acting in its typical capacity, i.e., as a surfactant. As discussed herein, the addition of the long polymer chain component to the network components imparts greater resilience and oil absorbing/containing capacity to the gel.

Compositions of the present invention may further include oil soluble film-forming agents, for example, high molecular weight silicones, such as dimethicone; polyurethanes; polyacrylates; and linear or branched polyhydrocarbons. The polyurethanes and the polyhydrocarbons also may function as spacers in the gel network. For example, polyglyceryl-2-diisostearate/IPDI copolymer, due to the presence of its many polar functional groups, such as —NH$_2$ and —C(O)O—, is capable of interacting (hydrogen-bonding) with the silica and the sugar fatty acid ester to form a gel network. However, as a result of its relatively short chain length, the resulting end product employing a gel network made with this polymer would be denser or less flexible as compared with the flexibility of a gel in which a longer chain polymer is used. If present, film formers are typically used in an amount of from 0 to about 20% by total weight of the composition.

The compositions of the present invention may also contain oil soluble active agents and skin conditioning agents. Non-limiting examples of these materials include antioxidants, ceramides, fatty acids, sunscreens, emollients, oil soluble vitamins and plant extracts, and the like. When used as the oil phase of an emulsion, the composition can also contain water soluble actives.

Depending upon its intended final use, the product may also contain a colorant. Any type of pigment, provided it is acceptable for use in the area to which the product will be applied, and with or without surface treatment, can be used in the product of the invention: examples of useful pigments include iron oxides (yellow, red, brown or black), titanium dioxide (white), zinc oxide, chrome oxide (green), chrome hydrate (green), ultramarines, manganese violet, ferric ferrocyanide, carmine 40, ferric ammonium ferrocyanide, or combinations thereof. Interference pigments, which are thin platelike layered particles having a high refractive index, which, at a certain thickness, produce interference colors, resulting from the interference of typically two, but occasionally more, light reflections, from different layers of the plate, can also be added to provide a pearlescence to the product, is such is desired. The composition may also contain one or more types of cosmetically acceptable glitter, i.e., particles of transparent or colored, solid organic materials, such as poly (ethylene terephthalate), polymethacrylate, and poly(vinyl-butyral), particles of metal, or particles of metal coated film or paper. Organic pigments may also optionally be included; these include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments, formed by the precipitation and absorption of organic dyes on an insoluble base, such as alumina, barium, or calcium hydrates. Particularly preferred lakes are primary FD&C or D&C Lakes and blends thereof. Stains, such as bromo dyes and fluorescein dyes can also be employed. Pigments when used are typically present in an amount of about 0.1 to about 30%, preferably about 0.1 to about 20%, by weight of the composition.

The gel system of the present invention may be used in the same manner as are other gelling systems in cosmetic compositions. Typical uses for gellant systems in cosmetics are structural support, prevention of liquid from flowing, controlled release of included agents, and the like. The gel system of the present invention provides all these functionalities, and may be used as a thickening component of any polar oil containing cosmetic, such as skin care creams, lotions, sticks or serums, as well as in color cosmetics, such as eyeshadows, blushes, mascaras, lipsticks, and the like. This polar-oil based gel can be used on its own, in an anhydrous product, or it can be used to thicken the oil phase of water and oil emulsion systems. The gel system is very useful as the base of a lip product. It has particular advantage when used in a moisturizing or shine-conferring top coat to a hydrocarbon- or silicone-based base coat (including, but not limited to, that described in U.S. Pat. No. 6,340,466 or 6,019,962, the contents of which are incorporated herein by reference) that may be matte, long-wearing, transfer resistant or drying, and may improve the wear of long-wearing or transfer resistant products. It may on its own also serve as a lipgloss, lip balm and soft gel lip color. In this context, it is useful in avoiding feathering that is so common in high shine lip products, as well as enhancing the wear and transfer resistance of the product itself as well as any transfer resistant base coat with which it is used.

The invention is further illustrated by the following non-limiting examples. Example 1. This example illustrates formulations of the compositions of the invention.

A.

| Material | Weight percent |
| --- | --- |
| Castor oil | 33.21 |
| Fumed silica | 1.79 |
| Sucrose acetate dibutyrate | 62.00 |
| Isopropylparaben/isobutyl-paraben/butylparaben | 0.10 |
| Polyglyceryl-2-diisostearate/IPDI copolymer | 2.00 |
| Vitamin E | 0.10 |
| Methyl glucose sesquistearate | 0.80 |

Preparation Procedure for Example 1A:
1) Fumed silica was added to a beaker and then Castor oil was slowly added to wet the silica;
2) A spatula was used to mix the silica and Castor oil well;
3) The mixture was homogenized (using a Silverson L4RT-A or a Greeco type homogenizer), until a well-dispersed mixture was obtained;
4) All ingredients were added, one by one, except for the methyl glucose sesquistearate, into another beaker with a prop mixer;
5) The temperature was set to about 60° C. with a mixing speed at about 60-80 rpm;
6) The system was mixed until completely clear;
7) The system was cooled down to a temperature of about 50° C.;
8) Methyl glucose sesquistearate was added and mixing was continued for at least 15 minutes;
9) The system was cooled to 30° C. or lower and discharged.

A clear viscous gel system was obtained. The viscosity was about 18,500 cps at room temperature after 24 hours.

B.

| Material | Weight percent |
| --- | --- |
| Sucrose polycottonseedate | 69.60 |
| Fumed silica | 2.25 |
| BHT | 0.05 |
| Isopropylparaben/isobutyl-paraben/butylparaben | 0.10 |
| Hydrogenated polyisobutene | 27.00 |
| Methyl glucose sesquistearate | 1.00 |

Preparation Procedure for Example 1B:
1) Fumed silica was added to a beaker and then sucrose polycottonseedate was added slowly to wet the silica;
2) A spatula was used to mix the silica and sucrose polycottonseedate well;
3) The mixture was homogenized (using a Silverson L4RT-A or Greeco type homogenizer), until a well-dispersed mixture was obtained;
4) BHT and preservatives were added along with the above silica/sucrose polycottonseedate mixture in another beaker and mixed with a prop mixer;
5) The temperature was set at about 70-75° C. and mixed at a speed of about 75-100 rpm;
6) Mixing continued until completely clear;
7) Hydrogenated polyisobutene was introduced into the system and mixing was continued until a uniform and clear system was obtained;
8) The mixture was cooled down to temperature about 50° C.;
9) Methyl glucose sesquistearate was introduced into the mixture and mixing was continued for at least 15 minutes or longer;
10) The system was cooled to 30° C. or lower and discharged.

A clear viscous gel system was obtained. The viscosity was about 21,000 cps at room temperature after 24 hours.

While the invention has been described in connection with preferred embodiments, it is not intended to limit the scope of the invention to the particular forms set forth but, on the contrary, it is intended to cover such alternatives, modifications, and equivalents as may be included within the spirit and scope of the invention as defined by the appended claims.

We claim:

1. A clear liquid gel composition for topical application to the skin, the composition comprising a polar oil, and a gellant system for the polar oil, the gellant system comprising a silica and a sugar fatty acid ester in a ratio of the silica to the sugar fatty acid ester in a range of from about 6:1 to about 1:5 and a long chain polymer having a molecular weight in a range of from about 400 to about 10,000 Daltons, a ratio of the silica to the long chain polymer being in the range of from about 1:2.5 to about 1:25, wherein particles of the silica are suspended and well-dispersed in the polar oil, the particles of silica associated with sugar rings of the sugar fatty acid ester serving as cross-linking centers, and alkyl groups of the sugar fatty acid ester entangled with the long chain polymer serving as spacers interconnecting the cross-linking centers so as to form a three-dimensional network having a crosslinking density sufficient to contain the polar oil.

2. The composition of claim 1 wherein the silica is a fumed silica.

3. The composition of claim 1 wherein the sugar fatty acid ester is a reaction product of a saturated or unsaturated $C_{12}$-$C_{36}$ fatty acid with a sugar or alkyl sugar in which the alkyl group contains from 1 to 8 carbon atoms.

4. The composition of claim 3 in which the fatty acid is a $C_{16}$-$C_{22}$ fatty acid.

5. The composition of claim 3 in which the sugar is a mono or oligosaccharide.

6. The composition of claim 5 wherein the sugar fatty acid ester is selected from the group consisting of sucrose monolaurate, glucose palmitate, alkylglucose sesquistearates, alkylglucose palmitates, PEG derivatives thereof, PPG derivatives thereof, and mixtures thereof.

7. The composition of claim 1 wherein the long chain polymer has a molecular weight in the range of from about 400 to about 6,000 Daltons.

8. The composition of claim 1 wherein the long chain polymer is a hydrocarbon polymer.

9. The composition of claim 8 wherein the hydrocarbon polymer is selected from the group consisting of linear or branched polybutene, polyisobutene, polyethylene, polydecene, hydrogenated derivatives thereof, copolymers thereof, and mixtures thereof.

10. The composition of claim 1 wherein the ratio of silica to sugar fatty acid ester is in the range of from about 3:1 to about 1:1.

11. The composition of claim 1 wherein a ratio of the silica to the long chain polymer is in the range of from about 1:5 to about 1:22.5.

12. The composition of claim 1 wherein the polar oil is selected from the group consisting of vegetable oils; triglycerides; esters having the formula RCO—OR', in which RCO is a carboxylic acid radical and OR' is an alcohol residue; polyol fatty acid polyesters derived from aliphatic or aromatic polyols having at least 4 free hydroxyl groups, at least 80% of the free hydroxyl groups being esterified with one or more fatty acids having from 8 to 22 carbon atoms; fatty alcohols, and mixtures thereof.

13. The composition of claim 1 which contains no wax or clay.

14. The composition of claim 1 which is a composition for application to the lips.

15. A gellant system for a polar oil, the gellant system comprising a silica and a sugar fatty acid ester in a ratio of the silica to the sugar fatty acid ester in a range of from about 6:1 to about 1:5, and at least one long chain polymer having a molecular weight in a range of from about 400 to about 10,000 Daltons, a ratio of the silica to the long chain polymer being range of from about 1:2.5 to about 1:25, wherein particles of the silica, when suspended and well-dispersed in the polar oil, associate with sugar rings of the sugar fatty acid ester and serve as cross-linking centers, and alkyl groups of the sugar fatty acid ester entangle with the long chain polymer and serve as spacers interconnecting the cross-linking centers so as to form a three-dimensional network having a crosslinking density sufficient to contain the polar oil.

* * * * *